(12) United States Patent
Peikoff (10) Patent No.: US 10,568,758 B1
(45) Date of Patent: Feb. 25, 2020

(54) PROPHYLACTIC DEVICE(S)

(71) Applicant: Michael Peikoff, Sarasota, FL (US)

(72) Inventor: Michael Peikoff, Sarasota, FL (US)

(73) Assignee: Michael Peikoff, Sarasota, FL (US)

( * ) Notice: Subject to any disclaimer, the term of this patent is extended or adjusted under 35 U.S.C. 154(b) by 0 days.

(21) Appl. No.: 16/294,551

(22) Filed: Mar. 6, 2019

Related U.S. Application Data (60) Provisional application No. 62/782,440, filed on Dec. 20, 2018.

(51) Int. Cl.
*A61F 6/04* (2006.01)

(52) U.S. Cl.
CPC .......... *A61F 6/04* (2013.01); *A61F 2006/044* (2013.01)

(58) Field of Classification Search
CPC .... A61F 6/00; A61F 6/005; A61F 6/02; A61F 6/04; A61F 2006/041; A61F 2006/043; A61F 2006/044; A61F 2006/045; A61F 2006/046; A61F 2006/047; A61F 2006/048; A61F 2006/049; A61F 5/453
USPC ........ 128/842, 844; 604/349, 350, 351, 352, 604/353
See application file for complete search history.

(56) References Cited

U.S. PATENT DOCUMENTS

| | | | | |
|---|---|---|---|---|
| 3,648,700 A | * | 3/1972 | Warner | A61F 6/04 128/844 |
| 4,074,712 A | * | 2/1978 | Wright | A61F 6/04 600/39 |
| 4,795,425 A | * | 1/1989 | Pugh | A61F 6/04 128/844 |
| 4,846,197 A | * | 7/1989 | Benjamin | A61F 6/04 128/844 |
| 4,869,723 A | | 9/1989 | Harmon | |
| 5,666,972 A | * | 9/1997 | Gifford | A61F 6/005 128/842 |
| 5,954,054 A | | 9/1999 | Johnson | |
| 6,145,507 A | | 11/2000 | Hardy | |
| 6,250,303 B1 | * | 6/2001 | Delaney | A61F 6/04 128/844 |

(Continued)

FOREIGN PATENT DOCUMENTS

| | | |
|---|---|---|
| JP | 2006-280622 A | 10/2006 |
| WO | WO-2014041534 A1 * | 3/2014 ............... A61F 6/04 |

OTHER PUBLICATIONS

International Search Report and Written Opinion for PCT/US2019/021130 dated May 14, 2019 (6 pages).

*Primary Examiner* — Victoria J Hicks
*Assistant Examiner* — Lindsay A Jeffries
(74) *Attorney, Agent, or Firm* — Shumaker, Loop & Kendrick, LLP (57) ABSTRACT

A condom and/or prophylactic device including an enclosed end configured to collect and securedly maintain bodily fluids and/or semen therein during intercourse; an open end that is spaced apart from the enclosed end that is further configured to receive a penis therethrough; and a main body positioned between and connected to the enclosed end and open end thereby forming a partial enclosure configured to receive and surround the penis therein and having an opening positioned mid-span along a length of the main body that is configured to allow skin on skin contact between the condom wearer and companion while in use.

14 Claims, 7 Drawing Sheets

(56) References Cited

U.S. PATENT DOCUMENTS

| | | | |
|---|---|---|---|
| 6,929,118 B1* | 8/2005 | Izz | A61F 6/005 206/69 |
| 2005/0095245 A1* | 5/2005 | Riley | A61K 9/0036 424/145.1 |
| 2013/0104904 A1* | 5/2013 | Hui | A61F 6/04 128/844 |
| 2016/0220412 A1* | 8/2016 | Vacco | A61F 6/04 |
| 2016/0287430 A1* | 10/2016 | Thomas | A61F 6/04 |
| 2018/0078406 A1* | 3/2018 | Wang | A61F 6/04 |

\* cited by examiner

PROPHYLACTIC DEVICE(S)

CROSS REFERENCE TO RELATED APPLICATION(S)

This U.S. Non-Provisional Patent Application claims priority from U.S. Provisional Patent Application No. 62/782,440 filed Dec. 20, 2018 entitled "Prophylactic Device(s)", which is incorporated by reference in its entirety herein.

TECHNICAL FIELD

The present invention relates generally to the field of prophylactic devices, and more particularly, to specialized prophylactic devices, such as condoms, having an internal check valve(s) positioned in a distal end of the device that forms a reservoir for receiving and retaining bodily fluids (e.g., ejaculate or semen) therein while the device is in use and further includes an opening positioned mid-span along the length of the device that allows for skin on skin (or skin on mucosa) contact while the device is in use thereby enhancing the user's sensation while maintaining the same degree of prevention of unplanned pregnancy and/or transmission of sexually transmitted disease(s) when compared to conventional devices.

BACKGROUND

Prophylactic devices such as condoms have been used over the past six decades as a means for birth control and to reduce or prevent the transmission of sexually transmitted diseases. While these devices have various different shapes, sizes, conformations, and thicknesses, there is a need to constantly improve prophylactic devices to further enhance ones sensations during sexual intercourse while concurrently maintaining the same level of reduction or prevention of sexually transmitted diseases and/or unplanned pregnancies currently obtained by conventional prophylactic devices.

SUMMARY

It is an object of the present disclosure to provide prophylactic devices/condoms that provide improved sensation over conventional prophylactic devices while maintaining the same degree of prevention for sexually transmitted diseases and/or unplanned pregnancy. To accomplish this feat, the devices and condoms disclosed herein utilize a novel and inventive configuration that includes an internal reservoir formed by a check valve, internal retention ring, and opening positioned mid-span along the length (of the main body) of the device/condom to advantageously achieve these desired results.

As disclosed further below, the internal reservoir formed by the check valve and internal retention ring maintains bodily secretions (e.g., ejaculate or semen) within an enclosed end of the device/condom while the opening positioned mid-span along the length (of the main body) of the device/condom allows for skin on skin (or skin on mucosa) contact between the device wearer and the wearer's partner. As disclosed further below, in certain aspects the device/condom is further configured to release spermicide, bactericide, and/or virucide from peripheral edges of the opening positioned mid-span along the length (of the main body) of the device/condom to further minimize and/or prevent transmission of sperm, bacteria, and/or viruses from the device wearer to the wearer's partner and/or vice versa.

Specifically, disclosed herein is a prophylactic device including an enclosed end configured to collect and maintain bodily secretions therein; an open end that is spaced apart from the enclosed end and is configured to receive male genitalia therethrough; and a hollow elastomeric main body positioned between and connected to the enclosed end and open end thereby forming a partial enclosure configured to receive and surround the male genitalia therein and having an opening positioned mid-span along a length of the main body that is configured to allow skin on skin (or skin on mucosa) contact while the prophylactic device is in use.

In certain aspects, the prophylactic device further includes a check valve formed within (e.g., integrally formed) and/or fixedly attached within the enclosed end that forms an internal reservoir within the enclosed end of the device that is configured to receive and maintain bodily secretions therein while the device is in use. The check valve passes the wearer's bodily fluids through an inlet into the internal reservoir and is further configured to prevent backflow out of the internal reservoir, thus retaining the bodily fluids therein.

In certain aspects, the prophylactic device further includes an internal retention ring formed on an inner surface of the hollow elastomeric main body that is positioned between the check valve and the opening positioned mid-span along the length of the main body, the internal retention ring extends inwardly within the hollow elastomeric main body to retain positioning of the device on the male genitalia and to further form a partition within the device that prevents any residual bodily secretion not maintained within the internal reservoir from entering the opening positioned mid-span along the length of the main body while the device is in use (and in certain aspects to further prevent entry of the head of the penis into the check valve).

In certain aspects, superabsorbent fibers line an internal surface of the hollow elastomeric main body between the check valve and the internal retention ring, the superabsorbent fibers/polymers configured to absorb residual bodily secretions not maintained within the internal reservoir while in use. Examples of superabsorbent fibers/polymers include, but are not limited to, a superabsorbent polymer formed from the polymerization of an acrylic acid blended with sodium hydroxide (also known as sodium polyacrylate or SAP), polyacrylamide copolymer, ethylene maleic anhydride copolymer, cross-linked carboxymethylcellulose, polyvinyl alcohol copolymers, cross-linked polyethylene oxide, starch grafted copolymer of polyacrylonitrile, or any combination thereof. The superabsorbent polymers used herein may be formed from any one of gel polymerization, solution polymerization, or suspension polymerization.

In certain aspects, the prophylactic device further includes an external retention ring positioned on an outermost peripheral edge of the open end, the external retention ring is more rigid than the hollow elastomeric main body and is configured to retain the device on the male genitalia while the device is in use.

In certain aspects, the hollow elastomeric main body is cylindrically shaped.

Also disclosed herein are condom(s) including: (a) an enclosed end configured to collect and securely maintain semen therein during intercourse; (b) an open end that is spaced apart from the enclosed end and is configured to receive a penis therethrough; and (c) a hollow elastomeric main body positioned between and connected to the enclosed end and open end thereby forming a partial enclosure configured to receive and surround the penis therein and having an opening positioned mid-span along a length of the main body that is configured to allow skin on skin contact between the condom wearer and companion.

In certain aspects, the condom further includes a check valve fixedly attached within the enclosed end that forms an internal reservoir within the enclosed end of the condom that is configured to receive and maintain semen therein during intercourse.

In certain aspects, the condom further includes an internal retention ring formed on an inner surface of the hollow elastomeric main body that is positioned between the check valve and the opening positioned mid-span along the length of the main body, the internal retention ring extends inwardly within the hollow elastomeric main body to retain positioning of the condom on the penis and to further form a partition within the condom that prevents any residual semen not maintained within the internal reservoir from entering the opening positioned mid-span along the length of the main body while the condom is in use.

In certain aspects, the condom includes superabsorbent fibers lining an internal surface of the hollow elastomeric main body between the check valve and the internal retention ring, the superabsorbent fibers configured to absorb residual semen not maintained within the internal reservoir while in use.

In certain aspects, the condom includes an external retention ring positioned on an outermost peripheral edge of the open end, the external retention ring is more rigid than the hollow elastomeric main body and is configured to retain the condom at a penis base while the condom is in use.

In certain aspects, the hollow elastomeric main body of the condom is cylindrical shaped.

In certain aspects, peripheral edges of the opening positioned mid-span along a length of the hollow elastomeric main body are configured to secrete a spermicide, bactericide, and/or virucide in a time released manner to further prevent and/or reduce the likelihood of transmission of sperm, bacteria, and/or virus(es) while the condom is in use.

In certain aspects, the internal reservoir of the condom includes a spermicide therein.

Also disclosed herein are kits including at least one of the prophylactic device(s) and/or condom(s) disclosed above and hermetically sealed packaging housing the device and/or condom therein. In certain aspects, a lubricant may be further included in the packaging therein that lubricates the device and/or condom thereby increasing shelf-life, as well as durability, of the device and/or condom. In certain aspects, various indicia are printed on the hermetically sealed package providing information regarding the condom and/or use thereof. In certain aspects, water based, silicone based, or oil based lubricants can be used, but in certain aspects, water or silicone base lubricants are especially preferred if the prophylactic device is latex based (acrylate based) because oil based lubricants will degrade the prophylactic device if the device is latex based.

Embodiments of the invention can include one or more or any combination of the above features and configurations.

Additional features, aspects, and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

FIGS. 1-10 depict the prophylactic device(s)/condom(s) 100 disclosed herein. As discussed above, it is an object of the present disclosure to provide prophylactic devices/condoms 100 that provide improved sensation over conventional devices while maintaining the same degree of prevention of sexually transmitted diseases and/or unplanned pregnancies obtained by conventional devices/condoms. To accomplish this feat, the devices/condoms 100 shown in FIGS. 1-10 utilize a novel and inventive internal reservoir 110 formed by a check valve 105 (i.e., a one-way valve), internal retention ring 130, and opening 125 positioned mid-span along the length (of the main body 120) of the device/condom. As disclosed further below, the internal reservoir 110 formed by the check valve 105 and internal retention ring 130 essentially maintain bodily secretions (e.g., ejaculate or semen) within an enclosed end 101 of the device/condom while the opening 125 positioned mid-span along the length (of the main body) of the device/condom allows for skin on skin (or skin on mucosa) contact between the device wearer and the wearer's partner.

Figure 1:
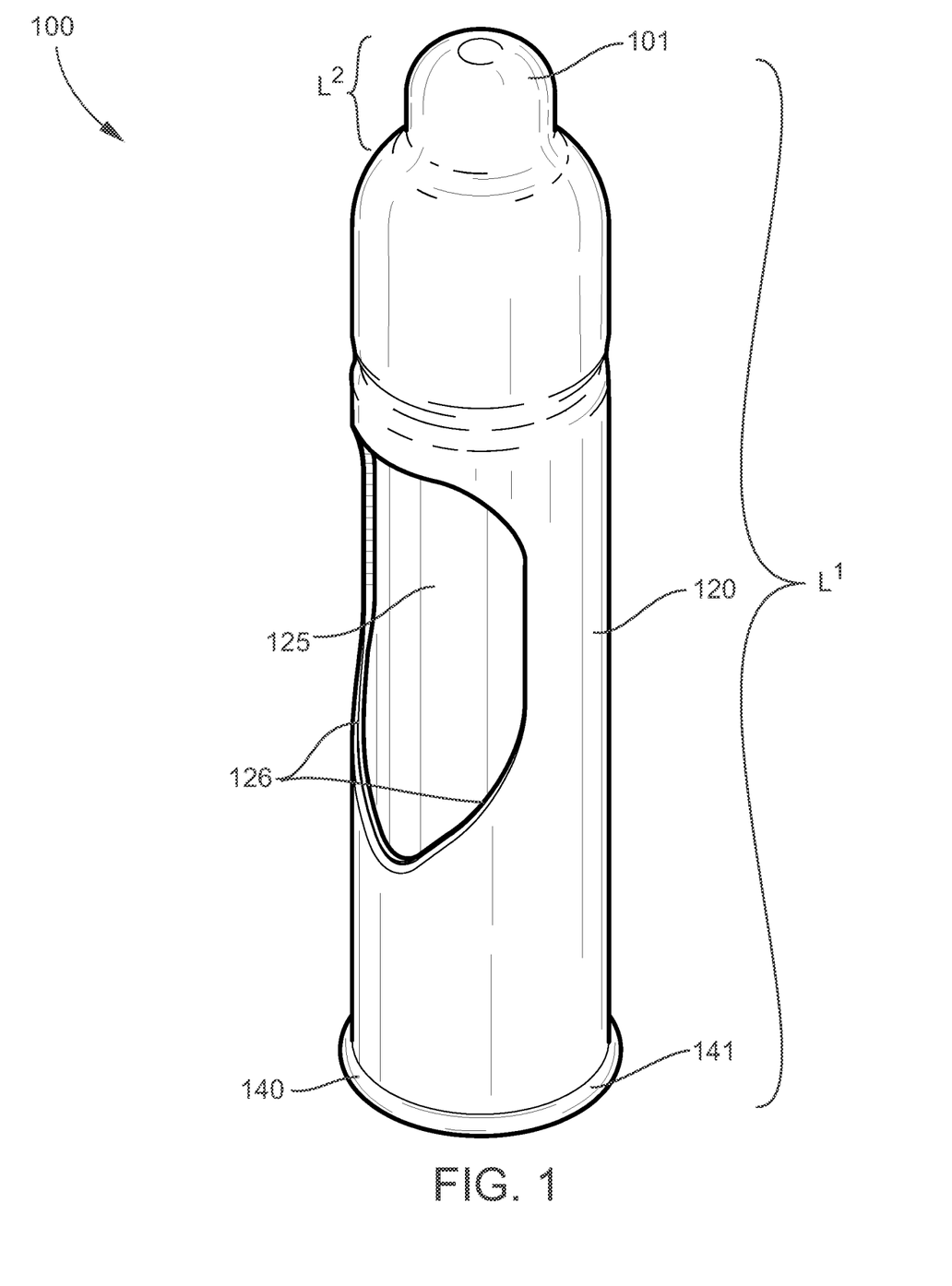
FIG. 1 is a first perspective view of the prophylactic device.
Figure 2:
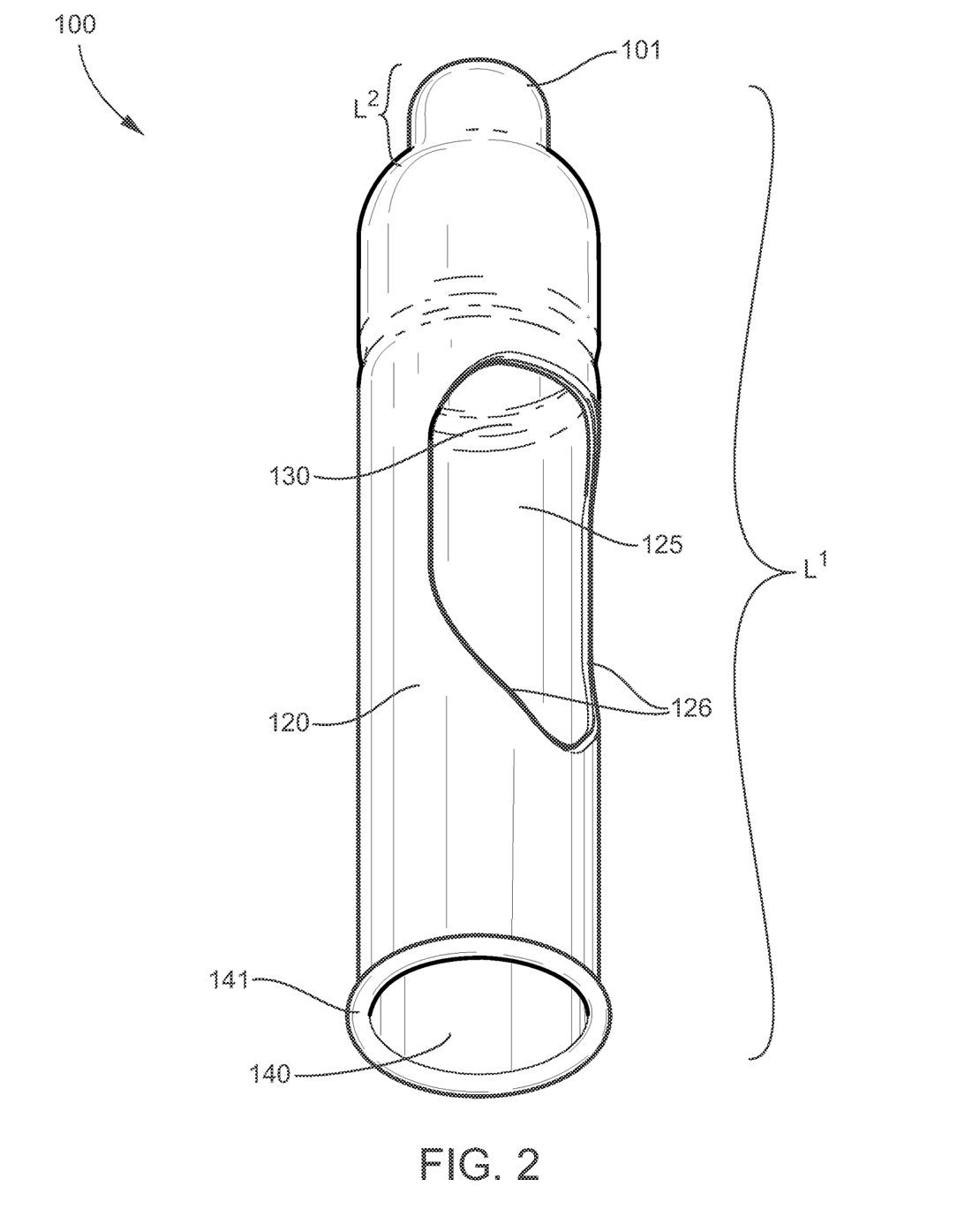
FIG. 2 is a second perspective view thereof.

With specific reference to FIGS. 1 and 2, FIGS. 1 and 2 depict two separate perspective views of the prophylactic device/condom 100 with $L^1$ being the longitudinal axis/length of the device/condom and $L^2$ corresponding to the exterior portions of the device corresponding to the internal reservoir 110 (discussed further below). In general, the devices/condoms disclosed herein have a predetermined shape (e.g., an elongate shape that can be cylindrical or semi-cylindrical) and an external tripartite configuration (three-part configuration) that includes an enclosed end 101 configured to collect and securely maintain bodily fluids (ejaculate or semen) therein during intercourse; an open end 140 that is spaced apart from the enclosed end and is configured to receive a penis therethrough; and a main body 120 (also referred to as an elastomeric hollow main body) positioned between and connected to the enclosed end 101 and open end 140 thereby forming a partial enclosure configured to receive and surround (e.g., circumferentially engage) the penis therein. The device/condom 100 further includes an opening 125 positioned mid-span along a length of the main body that is configured to expose a portion of the underside of the wearer's penis thereby allowing skin on skin (or skin on mucosa) contact between the device/condom wearer and companion to further enhance the wearer's pleasure while using the device/condom 100.

The exterior portions (enclosed end 101, main body 120, external retention ring 141) of the device/condom 100 are formed of a resiliently deformable, elastomeric material such as a natural rubber, a synthetic rubber (e.g., synthetic rubbers formed from polymers such as butadiene or copolymers such as acrylonitrile butadiene rubber), and/or other polymeric resin(s) such as acrylic and/or an acrylate material. The resiliently deformable elastomeric material is preferably hypoallergenic and non-immunogenic thereby reducing or completely avoiding any allergic and/or immune response of the device user and/or the user's partner while the user handles, wears, and/or uses the device/condom. As further shown, for example, in FIGS. 1, 2, and 8 certain exterior portions of the device/condom 100 vary in thickness relative to other portions of the device/condom. For example and as further shown in FIGS. 1, 2, and 8, external retention ring 141 is positioned/formed on one end of the device 100 and has a greater thickness than other external portions of the device/condom. The greater thickness of the external retention ring 141 reinforces this portion of the device and provides for greater strength, friction, and/or gripping potential in the portion of the device/condom thereby allowing the device to be securely retained on the wearer while in use.

Figure 3:
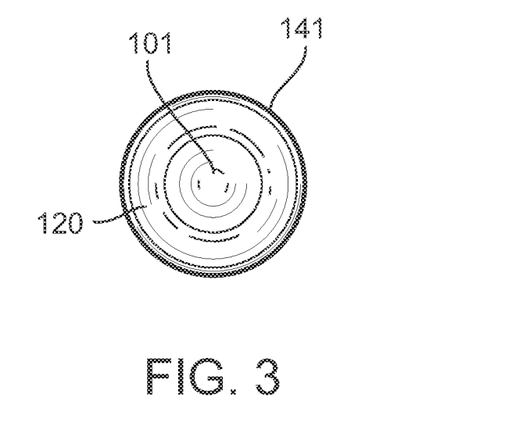
FIG. 3 is a front view thereof.
Figures 5, 6:
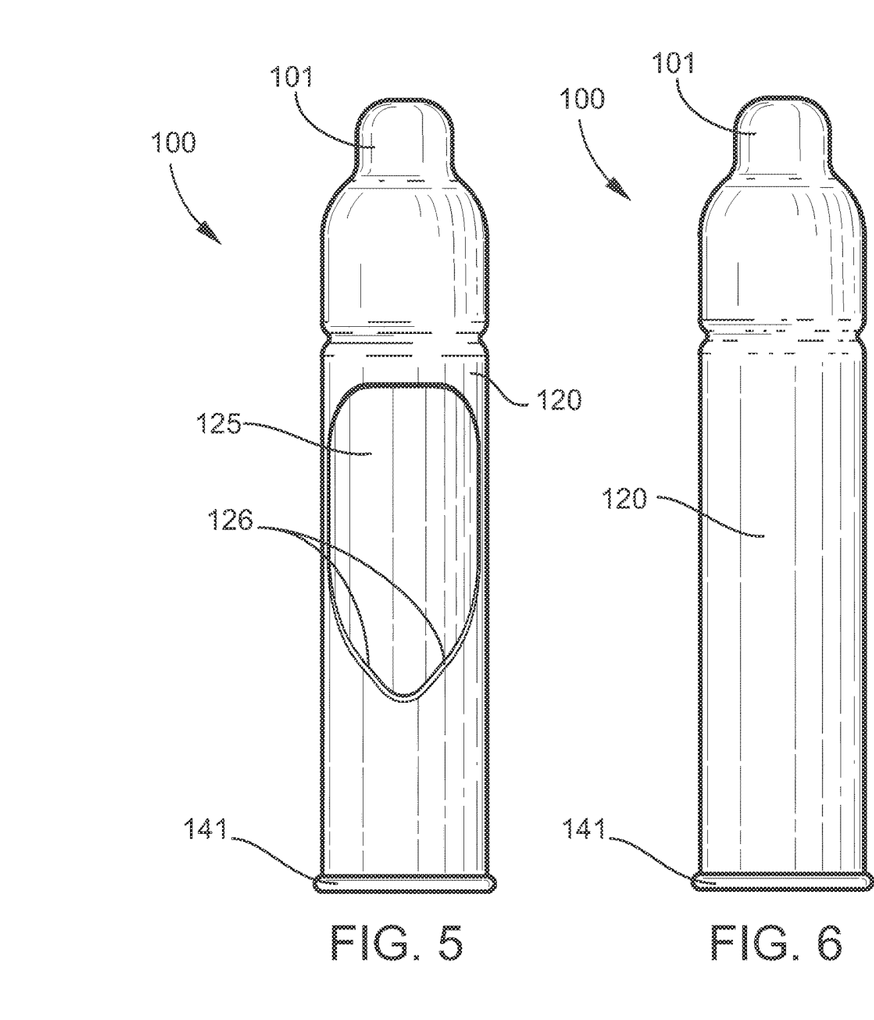
FIG. 5 is a bottom view thereof.
FIG. 6 is a top view thereof.
Figure 7:
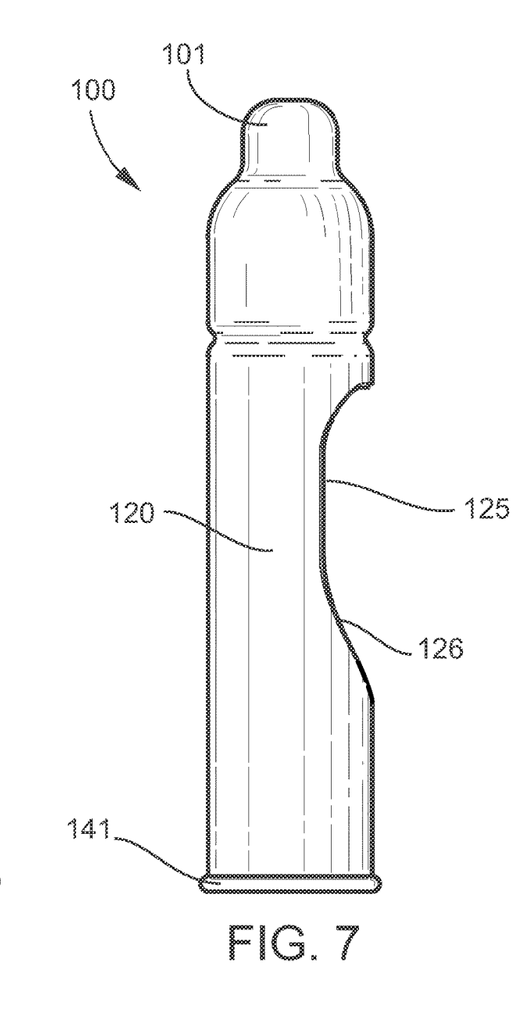
FIG. 7 is a right side view thereof, with the left side view being a mirror image thereof.
Figure 8:
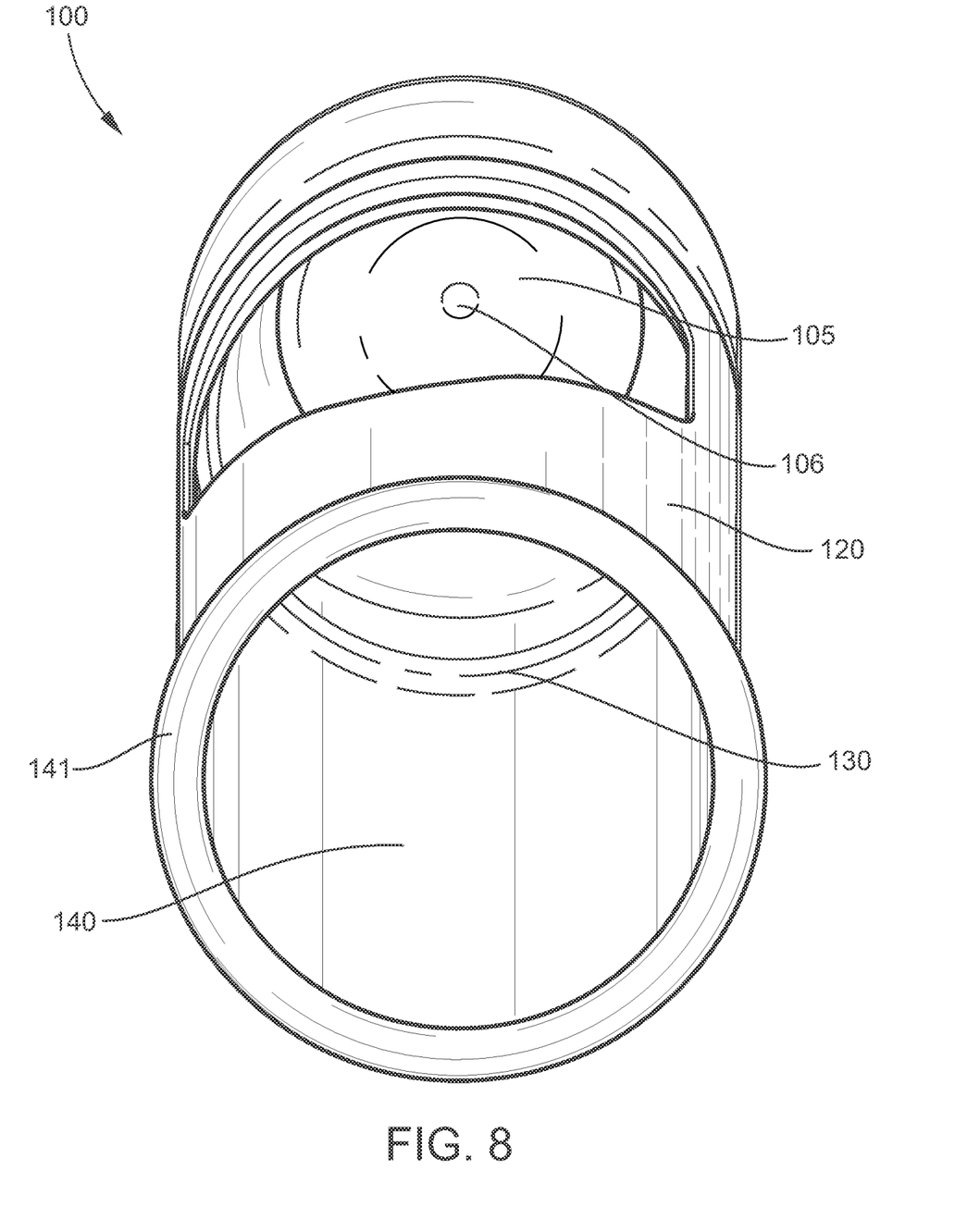
FIG. 8 is a third perspective view depicting inner portions of the device.

In addition to the above disclosures, FIGS. 3 and 5-7 also depict the exterior of the device/condom 100. For example, FIG. 3 depicts a front view of the device/condom with the enclosed end 101 being connected to the main body 120 such that the main body flares out therefrom (or slopes away from the enclosed end) along with the external retention ring 141. FIG. 5 further depicts a bottom view of the device/condom in which the enclosed end 101 is connected to the main body 120 and further depicts the opening 125 positioned mid-span along a length of the main body having a predetermined shape (e.g., a rectangular shape, a square shape, an ovoid shape, or a triangular shape) formed by peripheral edges 126 of the opening and the external retention ring 141 formed on the open end 140. FIG. 6 depicts a top view of the device/condom 100 that is identical to the bottom view of FIG. 5 with the exception that the top/top view of the device does not include an opening 125 positioned mid-span along a length of the main body. FIG. 7 depicts a right side view of the device/condom 100, with the left side view being a mirror image thereof. In particular, FIG. 7 depicts the enclosed end 101, main body 120, and external retention ring 141. FIG. 7 further depicts the opening 125 positioned mid-span along a length of the main body formed by peripheral edges 126 of the opening 125 forms a recessed portion relative to, for example, external retention ring 141 (i.e., the outer diameter of the external retention ring) and relative to the outer diameter portions of main body 120 that do not include opening 125. This configuration further increases exposure of the wearer's genitalia and further advantageously increases the wearer's pleasure while the device/condom is in use. For example, as further shown in FIG. 7, certain portions of peripheral edges 126 of the opening are sloped inwardly (e.g., a constant sloped gradient) towards inner portions of the device thereby increasing overall surface area of the opening, which increases exposure of the wearer's genitalia while the device is being worn/in use and further advantageously increases the wearer's pleasure while the device/condom is in use.

Figure 4:
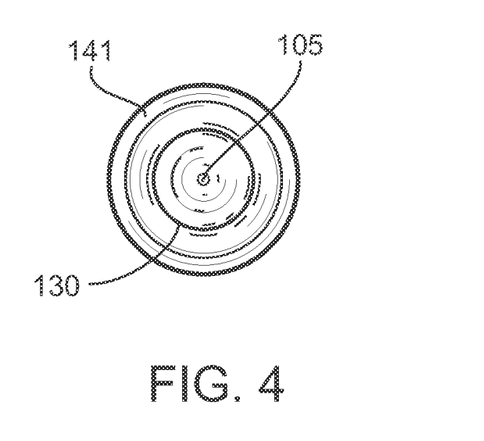
FIG. 4 is a back view thereof.

In view of the unique exterior of the device/condom 100, it should be further noted that the device/condom 100 disclosed herein also advantageously has a unique internal configuration for body fluid (e.g., ejaculate or semen) collection and retention therein while the device/condom is in use. Specifically, FIGS. 4 and 8-10 depict various views of the unique internal configuration of the device/condom 100. For example, FIG. 4 generally depicts a back view of the device/condom 100 further showing the internal configuration of the device/condom. In particular, FIG. 4 depicts the internal retention ring 130 and check valve 105.

Figure 9:
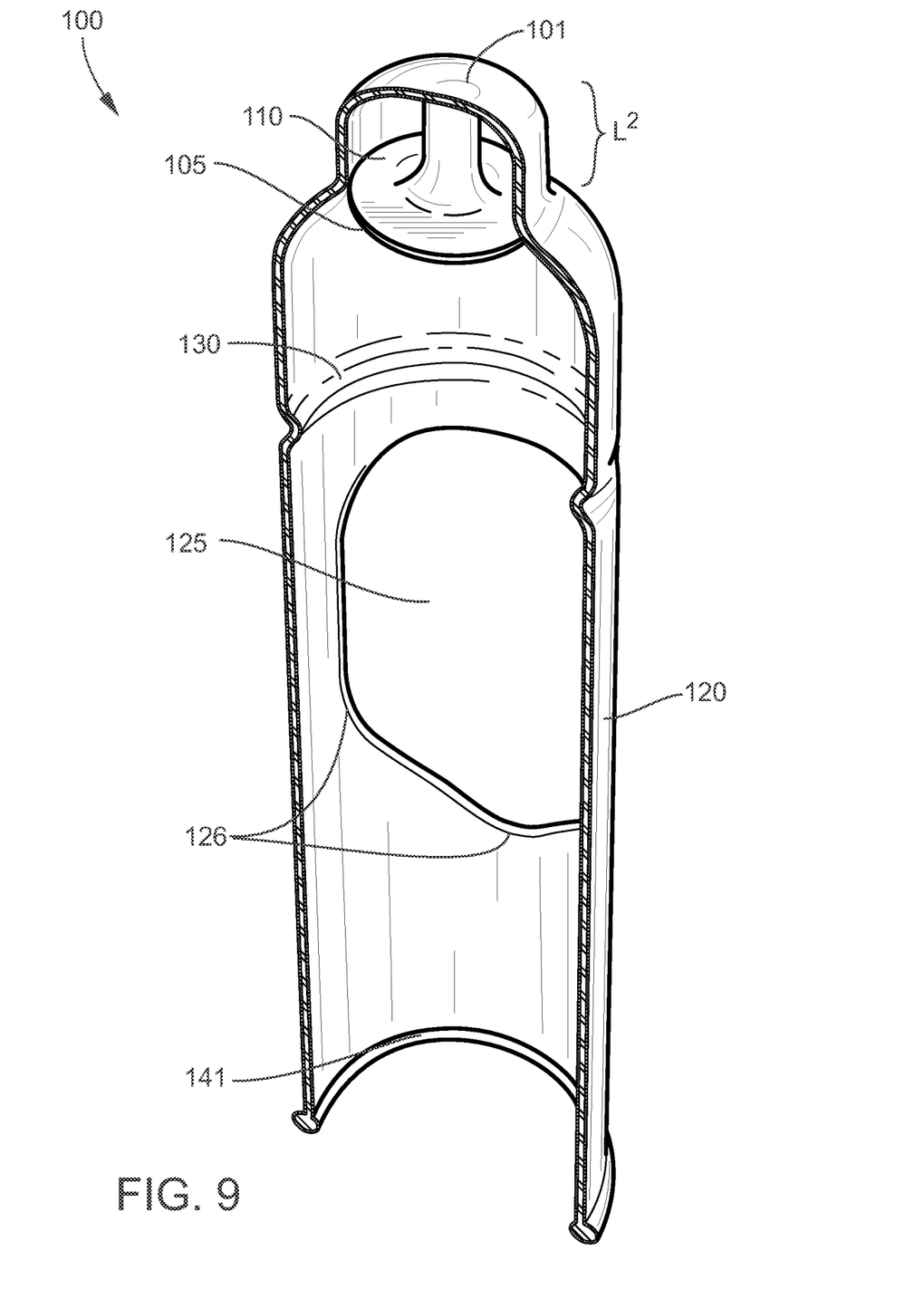
FIG. 9 is a first cross-section depicting a check valve/one-way valve positioned in an end of the device.
Figure 10:
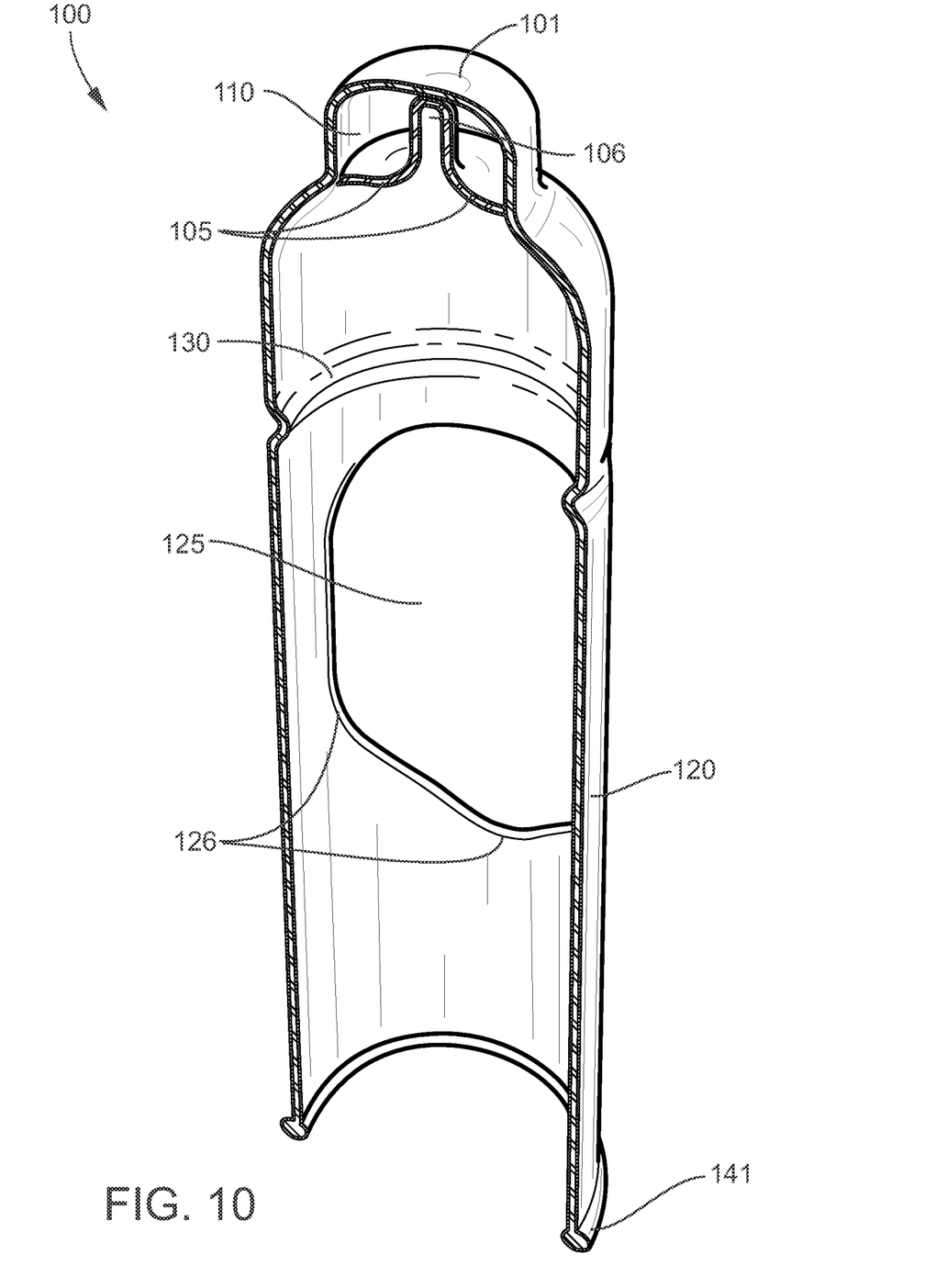
FIG. 10 is a second cross-section of the device further depicting the check valve/one-way valve positioned in an end of the device.

In view of FIG. 4, FIGS. 8-10 depict more detailed views of the internal configuration of the device/condom 100. Specifically, FIGS. 9 and 10 provide detailed cross-sections of the device/condom 100. For example, FIGS. 9 and 10 depict check valve 105 that is formed within (e.g., integrally formed within) and fixedly attached within the enclosed end 101 that forms an internal reservoir 110 within the enclosed end of the condom that is configured to receive and maintain semen therein during intercourse. In certain aspects, the check valve spans the entire inner diameter of the device and is partially or completely transverse to the longitudinal axis (L') of the device 100/hollow elastomeric main body 120 and has an opening configured to selectively pass semen/ejaculate therethrough into the reservoir 110 while concurrently preventing backflow of semen/ejaculate from the reservoir. In certain aspects and as further shown in FIGS. 9 and 10, first end portions of the check valve 105 are attached to the inner diameter of the hollow elastomeric main body while second end portions of the check valve extend upwardly away from the first end portions of the check valve that are attached to the inner diameter of the hollow elastomeric main body towards the enclosed end or the condom and converge with one another. In this aspect, the convergent ends form a check valve opening that selectively opens and closes to allow semen/ejaculate to flow therethrough into the reservoir 110 while the device is in use while concurrently preventing backflow of the semen/ejaculate from the reservoir. As further shown, for example in FIGS. 9 and 10, the check valve 105 may be conical or nipple shaped in which the wearer's penis is immediately adjacent to an inlet 106 of the check valve 105 while the device/condom 100 is in use. The check valve 105, and more particularly the inlet 106, is configured to receive and pass bodily fluids (e.g., ejaculate or semen) into the internal reservoir 110 and the check valve 105 further prevents and/or limits backflow therefrom.

As further shown in FIGS. 9 and 10, the device/condom 100 further includes an internal retention ring 130 formed on an inner surface of the main body 120 that is positioned between the check valve 105 and opening 125 positioned mid-span along the length of the main body 120. The internal retention ring 130 extends inwardly within the hollow elastomeric main body towards the center of the device and further functions to retain positioning of the device/condom 100 on the penis. In certain aspects, the internal retention 130 ring may be either continuously or discontinuously formed along the inner diameter of the main body 120, and in this aspect and as further shown in FIGS. 9 and 10, the continuous or discontinuous internal retention ring formed along the inner diameter of the main body 120 may further correspond to a continuous or discontinuous channel formed on the outer surface/outer diameter the device 100. While in certain preferred aspects, the internal retention ring 130 is continuously formed along the inner diameter of the main body 120 such that a partition is formed within the device/condom 100 by the internal retention ring 130 directly abutting the penis while the device/condom is in use thereby advantageously preventing any residual semen not maintained within the internal reservoir from entering the opening 125 positioned mid-span along the length of the main body. In certain aspects and to provide an added layer of protection, superabsorbent fibers/polymers lining an internal surface of the hollow elastomeric main body 120 between the check valve 105 and the internal retention ring 130 can be further included in the device/condom 100 that absorb residual bodily fluids (ejaculate of semen) not maintained within the internal reservoir while in use. Examples of superabsorbent fibers/polymers include, but are not limited to, a superabsorbent polymer formed from the polymerization of an acrylic acid blended with sodium hydroxide (also known as sodium polyacrylate or SAP), polyacrylamide copolymer, ethylene maleic anhydride copolymer, cross-linked carboxymethylcellulose, polyvinyl alcohol copolymers, cross-linked polyethylene oxide, starch grafted copolymer of polyacrylonitrile, or any combination thereof. The superabsorbent polymers used herein may be formed from any one of gel polymerization, solution polymerization, or suspension polymerization.

It should be further noted that spermicides, bactericides, and/or virucides may be included in various portions of the disclosed devices/condoms 100. For example, in certain aspects, peripheral edges 126 of the opening 125 positioned mid-span along a length of the hollow elastomeric main body 120 are configured to secrete a spermicide, bactericide, and/or virucide in a time released manner to further prevent and/or reduce the likelihood of transmission of sperm, bacteria, and/or virus(es) into and/or from the device/condom 100 while the device/condom is in use. For example, polymeric matrices, gels, and/or hydrogels loaded with spermicide, bactericide, and/or virucide may line the peripheral edges 126 of opening 125 and may be further configured to release the spermicide, bactericide, and/or virucide in a time released manner while the device/condom 100 is in use. In certain additional aspects, the internal reservoir 110 may further include a spermicide therein, and the internal portion of the device/condom 100 spanning from a lower portion of the check valve 105 to the internal retention ring may further include spermicide (and/or bactericides and/or virucides) therein to further prevent and/or reduce the likelihood of transmission of sperm, bacteria, and/or virus(es) while the device/condom 100 is in use.

The device/condom 100 disclosed herein may be further included in kits. For example, these kits include at least one of the prophylactic device(s) and/or condom(s) disclosed above and hermetically sealed packaging housing the device and/or condom therein. In certain aspects, a lubricant may be further included in the packaging therein that lubricates the device and/or condom thereby increasing shelf-life of the device and/or condom. In certain aspects, water based, silicone based, or oil based lubricants can be used, but in certain aspects, water or silicone base lubricants are especially preferred if the prophylactic device is latex based because oil based lubricants will degrade the prophylactic device if the device is latex based.

In certain aspects, various indicia are printed on the hermetically sealed package providing information regarding the device/condom 100 and/or use thereof. In certain additional aspects, the device/condom 100 may include indicia on the device itself further indicating how to use the device and the directionality/orientation of the device while in use. In certain additional aspects, the kit may further contain lubrication that is separately packaged from the condom/prophylactic device that may be further used during intercourse.

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

PARTS LIST

100 Condom/Prophylactic Device
101 Enclosed End
105 Check Valve
106 Inlet of check valve
110 Internal Reservoir
120 Hollow Elastomeric Main Body
125 Opening Positioned Mid-Span Along a Length of the Main Body
126 Peripheral Edges of Opening
130 Internal Retention Ring
140 Open End
141 External Retention Ring
$L^1$ Longitudinal Axis/Length of Condom/Prophylactic Device
$L^2$ Exterior Portion of Condom/Prophylactic Device Corresponding to Internal Reservoir

What is claimed is:

1. A condom comprising:
   (a) an enclosed end configured to collect and securely maintain semen therein during intercourse;
   (b) an open end that is spaced apart from the enclosed end and is configured to receive a penis therethrough;
   (c) a hollow elastomeric main body positioned between and connected to the enclosed end and open end thereby forming a partial enclosure configured to receive and surround the penis therein and having only a single, continuous opening formed by peripheral edges of the hollow elastomeric main body, the single, continuous opening positioned mid-span along a length of the main body such that peripheral edges of the single continuous opening are radially tapered towards a central longitudinal axis of the condom in an unrolled state and form a recessed portion relative to an external retention ring positioned on the condom and relative to an outer diameter of portions of the hollow elastomeric body that do not include the single continuous opening thereon, the single continuous opening configured to only expose a portion of an underside of a condom wearer's penis to allow skin on skin or skin on mucosa contact between the condom wearer and a companion, and
   (d) a check valve formed in the condom within the enclosed end that forms an internal reservoir within the enclosed end of the condom that is configured to receive and maintain semen therein during intercourse; and (e) an internal retention ring formed on an inner surface of the hollow elastomeric main body that is positioned between the check valve and the opening positioned mid-span along the length of the main body, the internal retention ring being more proximate to and positioned laterally adjacent to the opening positioned mid-span along the length of the main body than the check valve and the internal retention ring extends inwardly within the hollow elastomeric main body to retain positioning of the condom on the penis and to form a partition within the condom that prevents any residual semen not maintained within the internal reservoir from entering the opening positioned mid-span along the length of the main body while the condom is in use.

2. The condom of claim 1, wherein absorbent polymers/fibers line an internal surface of the hollow elastomeric main body between the check valve and the internal retention ring, the absorbent polymers/fibers configured to absorb residual semen not maintained within the internal reservoir while in use.

3. The condom of claim 2, wherein the external retention ring is positioned on an outermost peripheral edge of the open end, wherein the external retention ring is more rigid than the hollow elastomeric main body and is configured to retain the condom at a penis base while the condom is in use.

4. The condom of claim 3, wherein the hollow elastomeric main body is cylindrical shaped.

5. The condom of claim 4, wherein the peripheral edges of the opening positioned mid-span along the length of the hollow elastomeric main body are configured to secrete a spermicide, bactericide, and/or virucide in a time released manner to further prevent and/or reduce likelihood of transmission of sperm, bacteria, and/or virus(es) while the condom is in use.

6. The condom of claim 5, wherein the internal reservoir and the inner surface of the hollow elastomeric main body positioned between the check valve and the opening comprise a spermicide therein.

7. A prophylactic device comprising:
an enclosed end configured to collect and maintain bodily secretions therein;
an open end that is spaced apart from the enclosed end and is configured to receive male genitalia therethrough;
a main body positioned between and connected to the enclosed end and open end thereby forming a partial enclosure configured to receive and surround the male genitalia therein and having only a single continuous opening positioned mid-span along a length of the main body such that peripheral edges of the single continuous opening are radially tapered towards a central longitudinal axis of the prophylactic device in an unrolled state and form a recessed portion relative to an external retention ring positioned on the prophylactic device and relative to an outer diameter of portions of the main body that do not include the single continuous opening thereon, the single continuous opening is configured to only expose a portion of an underside of a wearer's penis to allow skin on skin contact while the prophylactic device is in use;
a check valve formed in the prophylactic device within the enclosed end that forms an internal reservoir within the enclosed end of the device that is configured to receive and maintain bodily secretions therein while the device is in use; and
an internal retention ring formed on an inner surface of the main body that is positioned between the check valve and opening positioned mid-span along the length of the main body, the internal retention ring being more proximate to and positioned laterally adjacent to the opening positioned mid-span along the length of the main body than the check valve and the internal retention ring extends inwardly within the main body to retain positioning of the device on the male genitalia and to further form a partition within the device that prevents any residual bodily secretion not maintained within the internal reservoir from entering the opening positioned mid-span along the length of the main body while the device is in use.

8. The device of claim 7, wherein absorbents fibers line an internal surface of the main body between the check valve and the internal retention ring, the absorbent fibers configured to absorb residual bodily secretions not maintained within the internal reservoir while in use.

9. The device of claim 8, wherein the external retention ring is positioned on an outermost peripheral edge of the open end, wherein the external retention ring is more rigid than the main body and is configured to retain the device on the male genitalia while the device is in use.

10. The device of claim 9, wherein the main body is cylindrically shaped.

11. The device of claim 10, wherein the peripheral edges of the opening positioned mid-span along the length of the main body are configured to secrete a spermicide, bactericide, and/or virucide in a time released manner while the device is in use.

12. The device of claim 11, wherein the internal reservoir comprises a spermicide therein.

13. A kit comprising:
(a) the condom of claim 1; and
(b) a hermetically sealed package housing the condom and optionally a lubricant therein that lubricates the condom.

14. The kit of claim 13, comprising the lubricant and further comprising indicia printed on the hermetically sealed package providing information regarding the condom.

\* \* \* \* \*